(12) United States Patent
Okazaki

(10) Patent No.: US 8,898,843 B2
(45) Date of Patent: Dec. 2, 2014

(54) ELECTRIC TOOTHBRUSH CAPABLE OF RECEIVING USER OPERATIONS

(75) Inventor: Tetsuzo Okazaki, Kyoto (JP)

(73) Assignee: Omron Healthcare Co., Ltd., Kyoto (JP)

(*) Notice: Subject to any disclaimer, the term of this patent is extended or adjusted under 35 U.S.C. 154(b) by 0 days.

(21) Appl. No.: 14/116,257

(22) PCT Filed: Jun. 1, 2012

(86) PCT No.: PCT/JP2012/064283
§ 371 (c)(1),
(2), (4) Date: Nov. 7, 2013

(87) PCT Pub. No.: WO2013/021716
PCT Pub. Date: Feb. 14, 2013

(65) Prior Publication Data
US 2014/0123414 A1  May 8, 2014

(30) Foreign Application Priority Data

Aug. 8, 2011  (JP) .................................. 2011-172623

(51) Int. Cl.
*A61C 17/22*  (2006.01)

(52) U.S. Cl.
CPC .................................. *A61C 17/221* (2013.01)
USPC ............... 15/22.1; 15/105; 345/156; 345/174

(58) Field of Classification Search
CPC ....................................................... G06F 3/044
USPC ............. 15/22.1, 105; 200/600; 345/156, 174
See application file for complete search history.

(56) References Cited

U.S. PATENT DOCUMENTS

| 5,353,468 | A | 10/1994 | Yap et al. |
| 5,784,742 | A * | 7/1998 | Giuliani et al. ................ 15/22.1 |
| 7,464,430 | B2 * | 12/2008 | Filsouf ........................... 15/22.1 |
| 7,661,172 | B2 * | 2/2010 | Hilscher et al. ................ 15/22.1 |

(Continued)

FOREIGN PATENT DOCUMENTS

| JP | A-60-114206 | 6/1985 |
| JP | A-61-232522 | 10/1986 |

(Continued)

OTHER PUBLICATIONS

International Search Report issued in International Patent Application No. PCT/JP2012/064283 dated Jul. 10, 2012.

*Primary Examiner* — Monica Carter
*Assistant Examiner* — Michael Jennings
(74) *Attorney, Agent, or Firm* — Oliff PLC

(57) ABSTRACT

An electric toothbrush includes a body portion, a portion of which is gripped by a user, and a brush part that is exchangeably attached to the body portion. The body portion includes a switch that is a contact-type sensor unit arranged on a portion that excludes the gripped portion, and that receives operations from the outside, and a control unit for controlling operations of the electric toothbrush in accordance with an operation received by the contact-type sensor unit. If a first operation is received by the contact-type sensor unit, the control unit outputs an indication that operations can be received for a certain time period, and if a second operation received by the contact-type sensor unit in the certain time period is an operation that corresponds to a predetermined operation pattern, the control unit controls operations of the electric toothbrush in accordance with the second operation.

8 Claims, 17 Drawing Sheets

(56) References Cited

U.S. PATENT DOCUMENTS

| | | | |
|---|---|---|---|
| 7,682,153 B2* | 3/2010 | Hilfinger et al. | 433/216 |
| 7,960,877 B2* | 6/2011 | Luo | 310/38 |
| 8,341,791 B2* | 1/2013 | Iwahori | 15/22.1 |
| 8,671,492 B2* | 3/2014 | Kressner | 15/22.1 |
| 8,683,635 B2* | 4/2014 | Jungnickel et al. | 15/22.1 |
| 2006/0037197 A1 | 2/2006 | Hawes et al. | |
| 2006/0096046 A1* | 5/2006 | Hilscher et al. | 15/22.1 |
| 2008/0060148 A1* | 3/2008 | Pinyayev et al. | 15/22.1 |
| 2008/0280248 A1* | 11/2008 | Pitts et al. | 433/32 |
| 2009/0038639 A1* | 2/2009 | Yetukuri et al. | 134/6 |
| 2009/0291422 A1* | 11/2009 | Puurunen et al. | 434/263 |
| 2010/0162500 A1* | 7/2010 | Hilscher et al. | 15/22.1 |
| 2011/0005015 A1 | 1/2011 | Iwahori et al. | |
| 2011/0010875 A1* | 1/2011 | Iwahori et al. | 15/22.1 |
| 2011/0012432 A1* | 1/2011 | Jung et al. | 307/104 |
| 2011/0265818 A1* | 11/2011 | Jungnickel et al. | 134/6 |
| 2011/0273153 A1* | 11/2011 | Lepper et al. | 323/282 |

FOREIGN PATENT DOCUMENTS

| | | |
|---|---|---|
| JP | A-5-235733 | 9/1993 |
| JP | A-2006-520212 | 9/2006 |
| JP | A-2009-217814 | 9/2009 |
| JP | A-2009-219756 | 10/2009 |
| JP | A-2010-266133 | 11/2010 |
| WO | WO 2009/013965 A1 | 1/2009 |

* cited by examiner

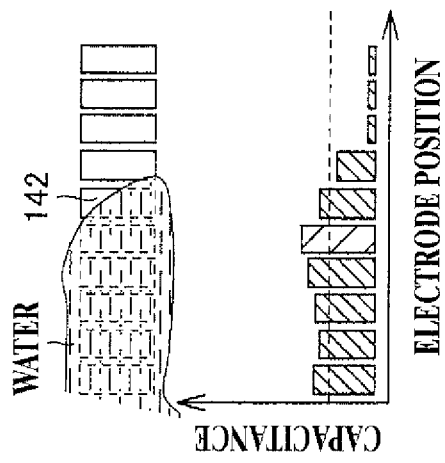
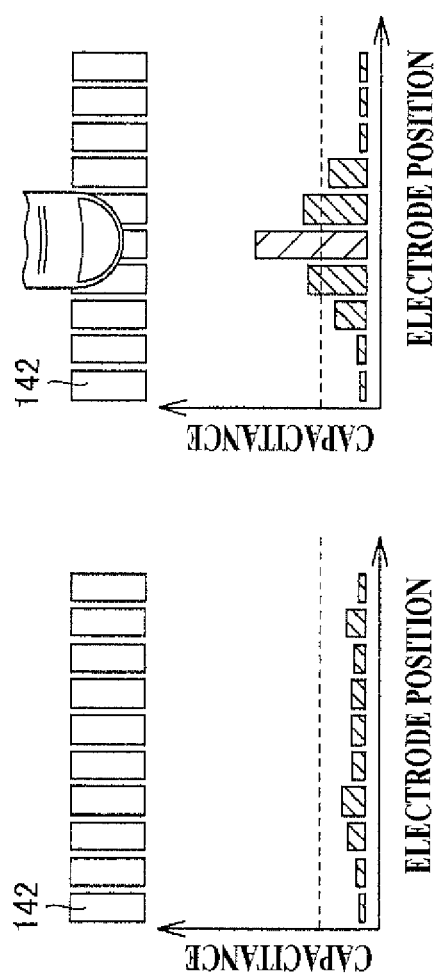
FIG. 20A  FIG. 20B  FIG. 20C

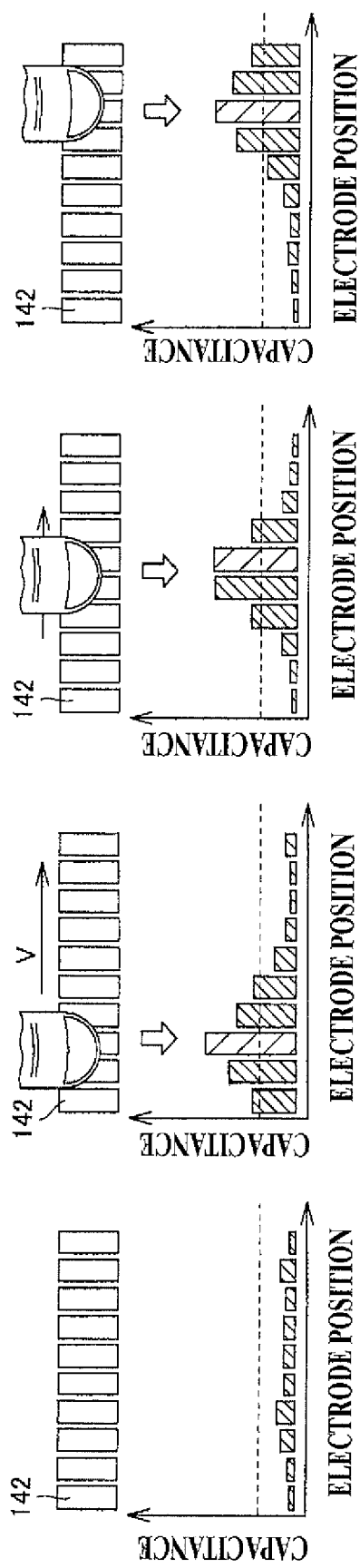

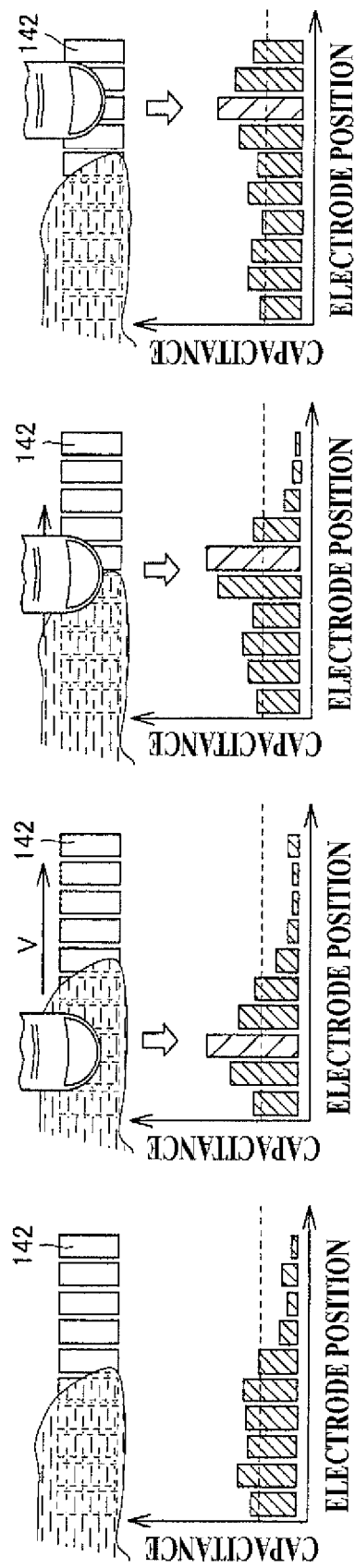

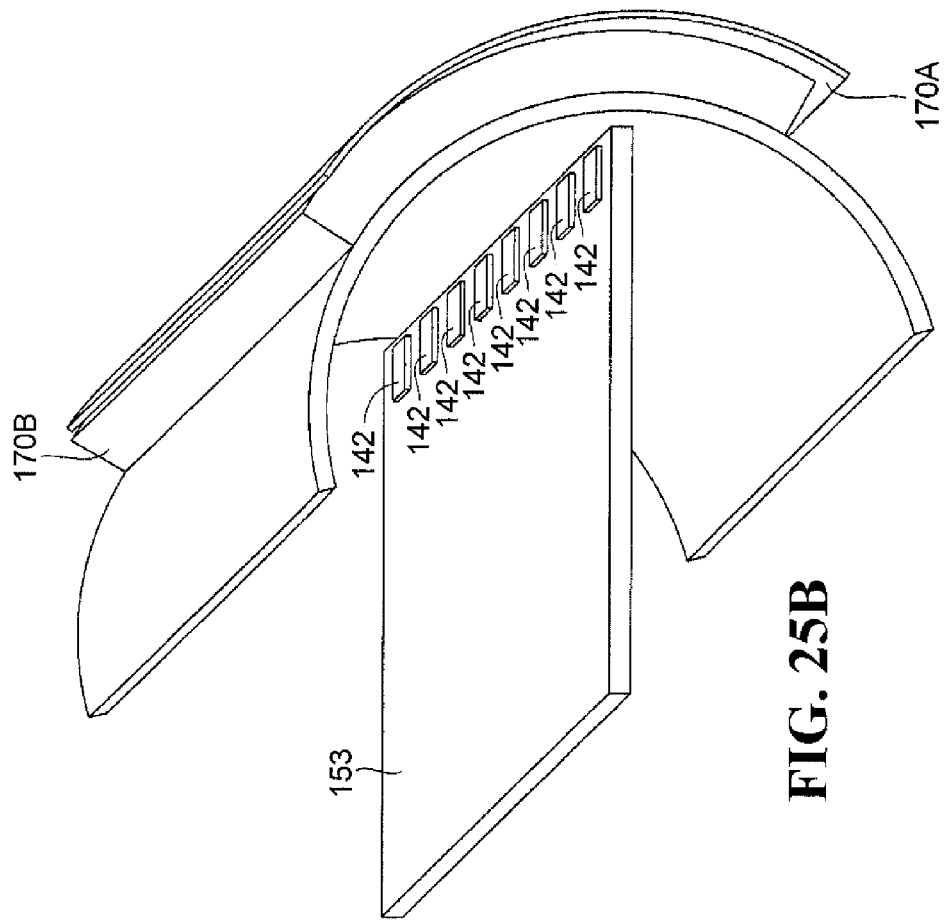
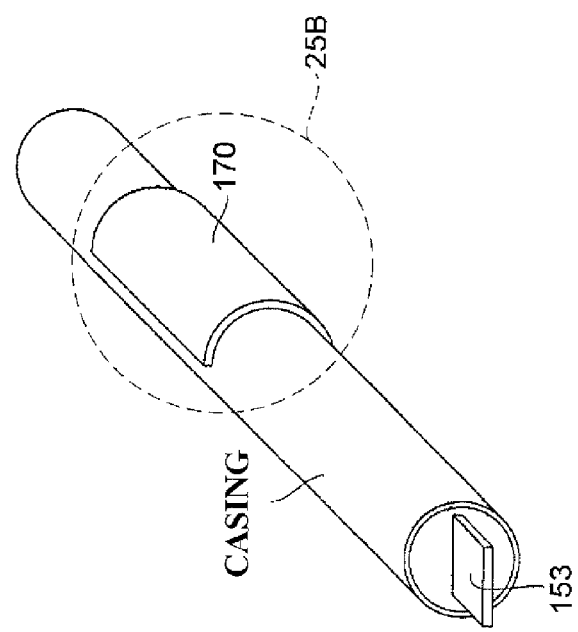

ELECTRIC TOOTHBRUSH CAPABLE OF RECEIVING USER OPERATIONS

TECHNICAL FIELD

The present invention relates to an electric toothbrush, and in particular relates to an electric toothbrush that includes a contact-type sensor unit that receives user operations.

BACKGROUND ART

Generally, electric toothbrushes often use a mechanical switch or the like on the casing of the electric toothbrush as an input apparatus for receiving user operations. However, when a mechanical switch is used, a gap is formed between the switch unit and the casing, thus allowing foreign matter to accumulate in the gap and making cleaning difficult. Also, since space is necessary in order to dispose the mechanical switch, it is difficult to dispose the switch in a narrow portion of the casing and in a portion where other parts are disposed.

Capacitance-type touch switches and the like have been used as the input apparatus in order to resolve this problem. With this technique, electrodes are provided inside the casing, thus making it possible to separate the interior and exterior of the casing so as to achieve good waterproofing, and cost is suppressed since there is no need for fabrication or additional mechanical parts.

Examples in which a capacitance-type input apparatus is applied to a handheld device include the toothbrush with electronic melody generator in Patent Literature 1 (JP S60-114206A), the handheld instrument in Patent Literature 2 (JP 2006-520212A), and the personal care device provided with capacitive on/off switch in Patent Literature 3 (JP H5-235733A).

Since change in capacitance is used as input with a capacitance-type input apparatus, a false operation is performed when the input apparatus of a handheld device is unintentionally touched when repositioning the casing portion in the hand.

As methods for avoiding false operations due to unintentional touch, examples of methods for rejecting or recognizing input at one site based on input at another site include the method proposed in Patent Literature 4 (JP 2009-217814A) for selectively rejecting touch contact in an edge region of the touch surface, and the heating cooker proposed in Patent Literature 5 (JP 2010-266133A).

CITATION LIST

Patent Literature

Patent Literature 1: JP S60-114206A
Patent Literature 2: JP 2006-520212A
Patent Literature 3: JP H5-235733A
Patent Literature 4: JP 2009-217814A
Patent Literature 5: JP 2010-266133A

SUMMARY OF INVENTION

Technical Problem

If the above-described methods for avoiding false operations caused by unintended touch are applied to an electric toothbrush, the user needs to select a specific site while viewing the input apparatus. However, since the input apparatus is generally provided on the handle portion of an electric toothbrush, it is difficult for the user to view the input apparatus during the tooth-brushing operation since the user grips the handle portion with their hand, and the handle portion is close to their face. Accordingly, it is difficult for the above-described methods for avoiding false operations caused by unintended touch to be applied to electric toothbrushes.

In view of this, an object of the present invention is to provide an electric toothbrush that includes a contact-type sensor unit as an operation unit, judges whether or not input was intended, and performs operation accordingly.

Solution to Problem

An electric toothbrush according to the present invention includes a body portion, a portion of which is gripped by a user, and a brush portion that is exchangeably attached to the body portion.

The body portion includes a contact-type sensor unit that is arranged on a portion of the body portion that excludes the gripped portion, and is for receiving an operation from the outside, and a control unit for controlling operation of the electric toothbrush in accordance with the operation received by the contact-type sensor unit.

In a case where a first operation is received by the contact-type sensor unit, the control unit outputs an indication that an operation can be received for a certain time period, and in a case where a second operation received by the contact-type sensor unit in the certain time period is an operation that corresponds to a predetermined pattern, the control unit controls operation of the electric toothbrush in accordance with the second operation.

Advantageous Effects of Invention

According to the present invention, an electric toothbrush includes a contact-type sensor unit for receiving operations from the outside, judges whether or not an operation performed via the contact-type sensor unit is an intended input operation, and performs operation control accordingly.

BRIEF DESCRIPTION OF DRAWINGS

FIGS. 20A, 20B and 20C are diagrams showing examples of the detection of the operation type based on change in the capacitance values of a row of input electrodes according to the embodiment.

FIGS. 21A, 21B, 21C and 21D are diagrams showing examples of the detection of the operation type based on change in the capacitance values of a row of input electrodes according to the embodiment.

FIGS. 22A, 22B, 22C and 22D are diagrams showing examples of the detection of the operation type based on change in the capacitance values of a row of input electrodes according to the embodiment.

FIGS. 25A and 25B are diagrams illustrating a function for preventing the influence of water on the electrode portion according to the embodiment.

DESCRIPTION OF EMBODIMENTS

An embodiment of the present invention will be described in detail below with reference to the drawings. Note that like reference signs in the figures denote the same or corresponding portions.

Although an electric toothbrush having a brush provided on the surface of a casing is described in the present embodiment, the configuration of the present embodiment can be generally applied to apparatuses that can be used in oral care (tooth cleaning, brushing, gum massage, and the like). Specifically, the configuration of the present embodiment can be applied to an apparatus that, rather than using a toothbrush as the member for oral care, uses a resin part that employs a sponge, rubber, an elastomer or the like, or uses an oral care member obtained by combining a brush and any of such resin parts.

Configuration

The configuration of the electric toothbrush will be described below with reference to FIGS. 1 to 3.

Figure 1:
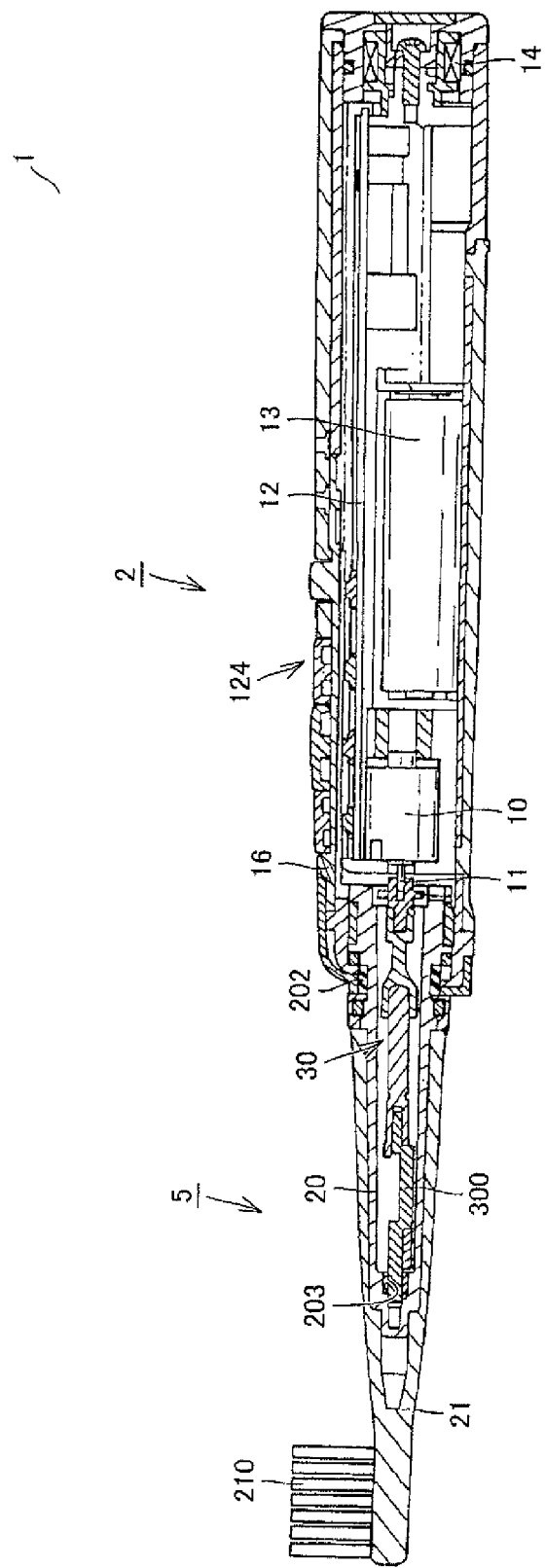
FIG. 1 is a cross-sectional view of an example of an internal configuration of an electric toothbrush according to an embodiment.
Figure 2:
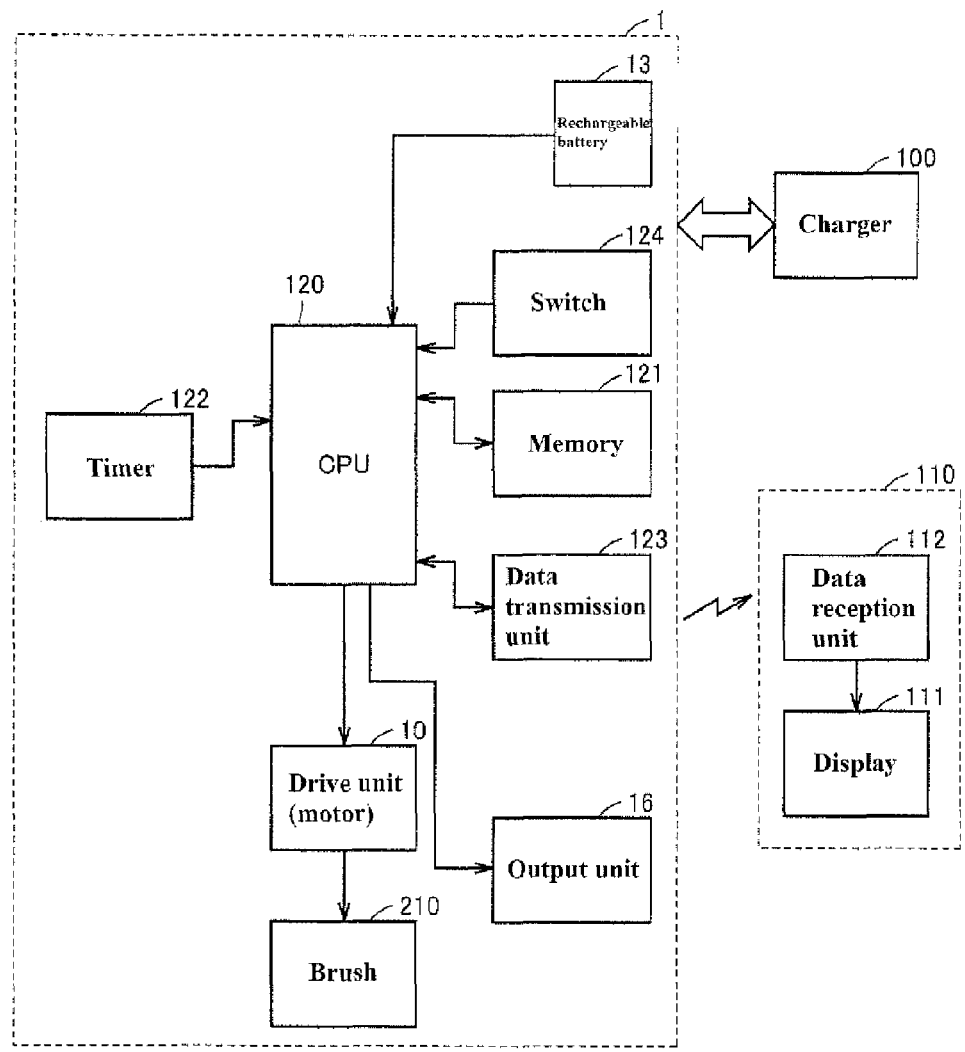
FIG. 2 is a block diagram showing a system including the electric toothbrush according to the embodiment.
Figure 3:
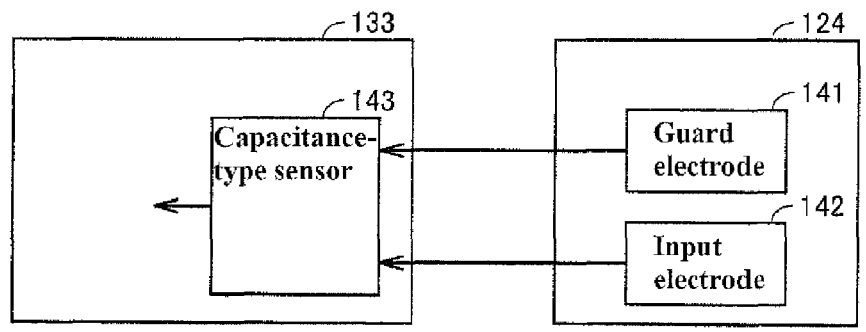
FIG. 3 is a diagram illustrating a configuration of a switch according to the embodiment.

FIG. 1 is a cross-sectional view of an example of the internal configuration of the electric toothbrush, FIG. 2 is a block diagram showing a system that includes the electric toothbrush, and FIG. 3 is a diagram for describing a switch 124 of the electric toothbrush in relation to peripheral units.

An electric toothbrush 1 includes a body portion 2 with a built-in motor 10 as the drive source, and a vibrating member 5 that vibrates when driven by the motor 10. Accordingly, the rotation frequency of the motor 10 corresponds to the vibration frequency of the electric toothbrush body. The body portion 2 has a substantially columnar casing, and a portion of the casing also serves as a handle portion that is gripped (i.e., held in the hand) by a user during brushing of the teeth.

Furthermore, in relation to the electric toothbrush 1, a charger 100 is provided to hold the body portion 2 and charge the electric toothbrush 1 while it is held therein, and an indicator 110 for outputting various types of information such as brushing results.

The casing of the body portion 2 is provided with the switch 124 for receiving operations from the outside for, for example, instructing the power to be turned on/off and instructing a switch in later-described operation modes of the motor 10. The casing of the body portion 2 is also internally provided with a rechargeable battery 13, a charging coil 14, and the like. The rechargeable battery 13 is a power source with a rated output of 2.4 V for supplying power to various units such as the motor 10 (e.g., a direct current motor) and a drive circuit 12. The rechargeable battery 13 is contactlessly charged through electromagnetic induction when the body portion 2 is merely held in the charger 100. The drive circuit 12 has a CPU (Central Processing Unit) 120 that is mounted on a substrate (not shown), performs various types of arithmetic operations, and executes control, a memory 121 that stores programs and various types of setting values, a timer 122, a data transmission unit 123, and the like. The data transmission unit 123 performs wireless communication with a data reception unit 112 of the indicator 110. The indicator 110 includes a display 111 for outputting data such as brushing results received by the data reception unit 112.

Also, the body portion 2 integrally includes an output unit 16 for outputting an indication that the switch 124 can receive operations. The output unit 16 includes an audio output unit (buzzer or speaker), a light (LED (Light Emitting Diode) or the like), or the like.

The vibrating member 5 includes a stem portion 20 that is fixed to the body portion 2, and a brush part 21 that is attached to the stem portion 20. A brush 210 is provided on the tip of the brush part 21. Since the brush part 21 is a consumable part, it is configured so as to be removable from the stem portion 20 for replacement with a new part.

The brush part 21 of the vibrating member 5 includes a brush portion on which the brush 210 is arranged, and a handle portion located on the body portion 2 side. Note that the handle portion may be configured so as to be entirely or partially included in the body.

The stem portion 20 is made of a resin material. The stem portion 20 is attached to the body portion 2 via an elastic member 202 made of an elastomer. The stem portion 20 is a tube-shaped member that is closed at the tip (end portion on the brush side), and has a bearing 203 at the tip inside the tube. The tip of an eccentric shaft 30 that is coupled to a rotation shaft 11 of the motor 10 is inserted into the bearing 203 of the stem portion 20. The eccentric shaft 30 has a weight 300 in the vicinity of the bearing 203, and the center of gravity of the eccentric shaft 30 is displaced from its center of rotation. Note that a very small clearance is provided between the tip of the eccentric shaft 30 and the bearing 203.

During operation, the CPU 120 supplies the motor 10 with a drive signal (e.g., a PWM (Pulse Width Modulation) signal) that corresponds to the operation mode, and thus the motor 10 rotates, and the rotation shaft 11 rotates in conjunction. The eccentric shaft 30 also rotates along with the rotation of the rotation shaft 11, and since the center of gravity of the eccentric shaft 30 is displaced, it moves so as to swing around the center of rotation. Accordingly, the movement of the tip of the eccentric shaft 30 is transmitted to the inner wall of the bearing 203, and the stem portion 20 and the brush part 21 attached thereto can be vibrated (moved) at a high speed.

The user brushes their teeth by pressing the vibrating brush 210 against their teeth while holding a portion of the casing of the body portion 2.

The configuration of the switch 124 will be described below with reference to FIG. 3. The switch 124 is a contact-type sensor and has an electrode portion. The electric toothbrush 1 has a capacitance-type sensor 143 for measuring the capacitance value of the electrode portion. The electrode portion has a guard electrode 141 and an input electrode 142. The guard electrode 141 is arranged so as to surround the input electrode 142.

The capacitance-type sensor 143 is provided as one of the functions of a later-described operation reception unit 133. When a conductor such as a portion of the body comes into contact with (touches) the electrodes during operation, the capacitance between the conductor and the electrodes is measured by the capacitance-type sensor 143. Whether or not contact was made is determined based on the measured value.

Although the electrode portion includes both the guard electrode 141 and the input electrode 142 in the present embodiment in order to raise the accuracy of the operation determination, the electrode portion may include only the input electrode 142.

Figure 4:
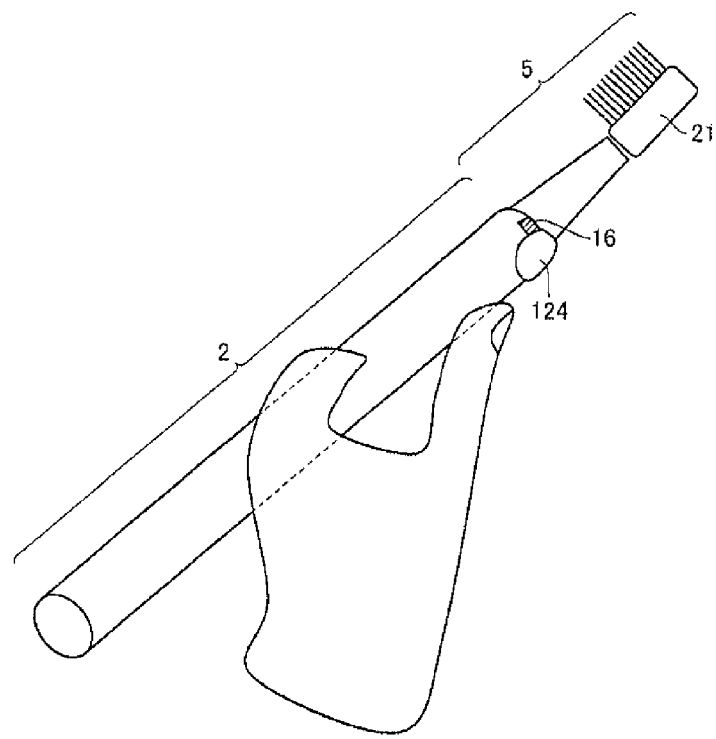
FIG. 4 is a diagram showing an example of the arrangement of the switch and an output unit on a casing of a body portion according to the embodiment.

FIG. 4 shows an example of the arrangement of the switch 124 and the output unit 16 on the casing of the body portion 2. In the present embodiment, the switch 124 is arranged on a portion of the casing of the body portion 2 that excludes the portion that is gripped during brushing. Also, if the output unit 16 performs output using audio or a light, the output unit 16 is also provided on a portion of the body portion 2 that excludes the gripped portion.

FIG. 4 shows that since the portion where the switch 124 is arranged on the surface of the columnar casing of the body portion 2 is an end portion on the side where the body portion 2 and the vibrating member 5 are joined, operating the switch 124 requires the user to intentionally extend a finger that is gripping the body portion 2 during brushing, thus making it possible to avoid unintended contact with the switch 124. Also, since the switch 124 is provided on the body portion 2, the vibration of the vibrating member 5 is not hindered by operations.

Figure 5:
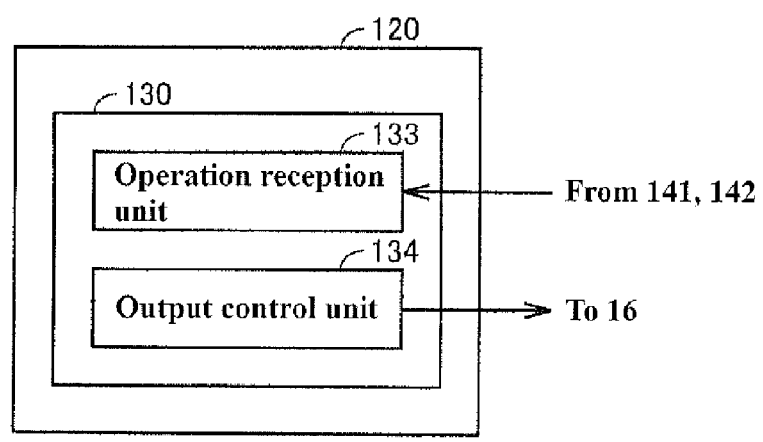
FIG. 5 is a configuration diagram of functions for controlling the electric toothbrush in accordance with switch operations according to the embodiment.

FIG. 5 is a configuration diagram of functions for electric toothbrush control performed in accordance with operations performed on the switch 124 according to the present embodiment. As shown in FIG. 5, the CPU 120 includes a control unit 130 for controlling operation of the electric toothbrush 1 in accordance with the content of operations received due to the switch 124 being touched. The control unit 130 has the operation reception unit 133 and an output control unit 134. If the switch 124 received an operation, the output control unit 134 controls the output unit 16 so as to output an indication that operations can be received for a certain time period. The output control unit 134 controls the output of audio, the blinking or lighting of a light, or the like by the output unit 16.

Although the output control unit 134 controls the operation of the output unit 16 here, a configuration is possible in which it controls the rotation of the motor 10 so as to change the vibration (movement) mode of the brush part 21.

Although the functions shown in FIG. 5 are provided by a combination of circuitry and a program executed by the CPU 120, they may be provided by only a program, or by only circuit parts.

Figure 6:
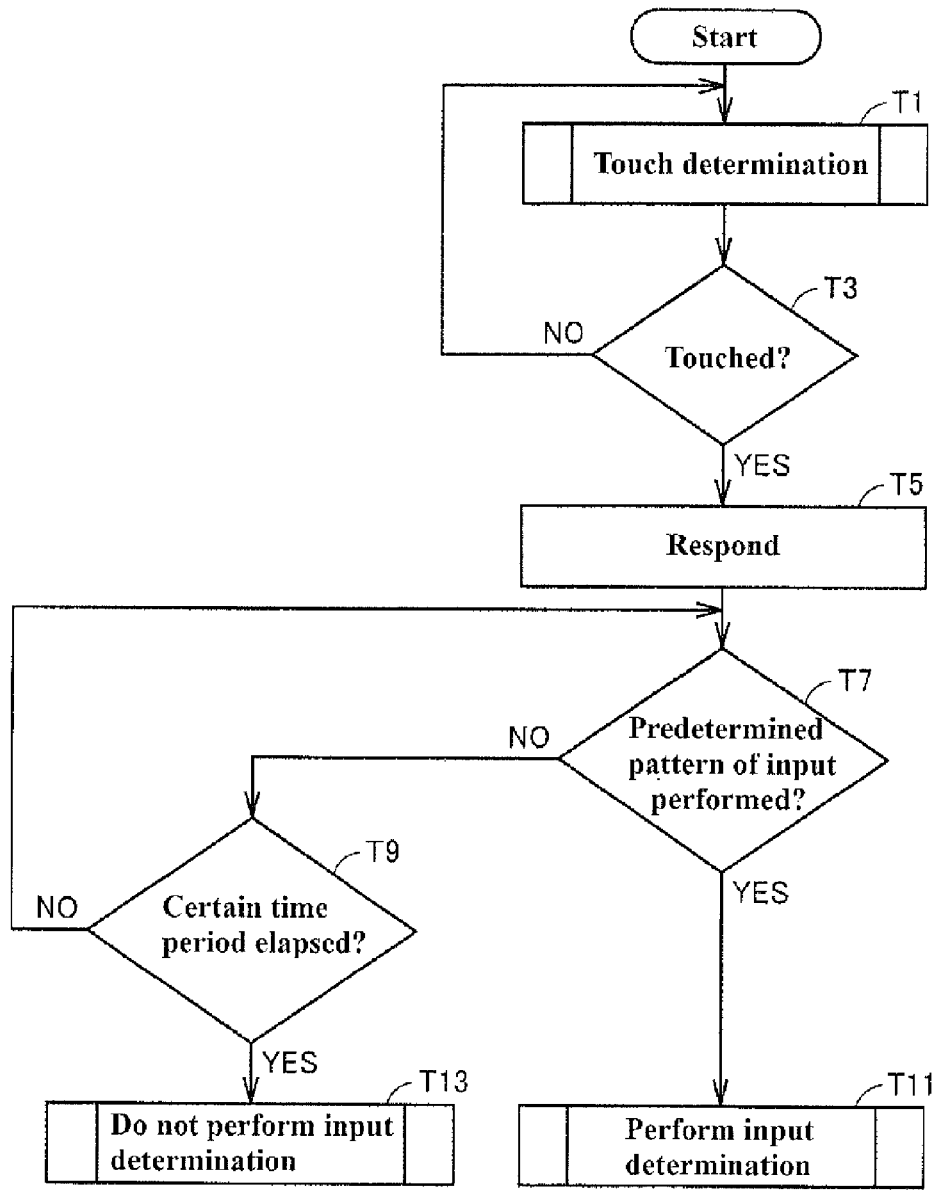
FIG. 6 is a flowchart of processing according to the embodiment.
Figure 7:
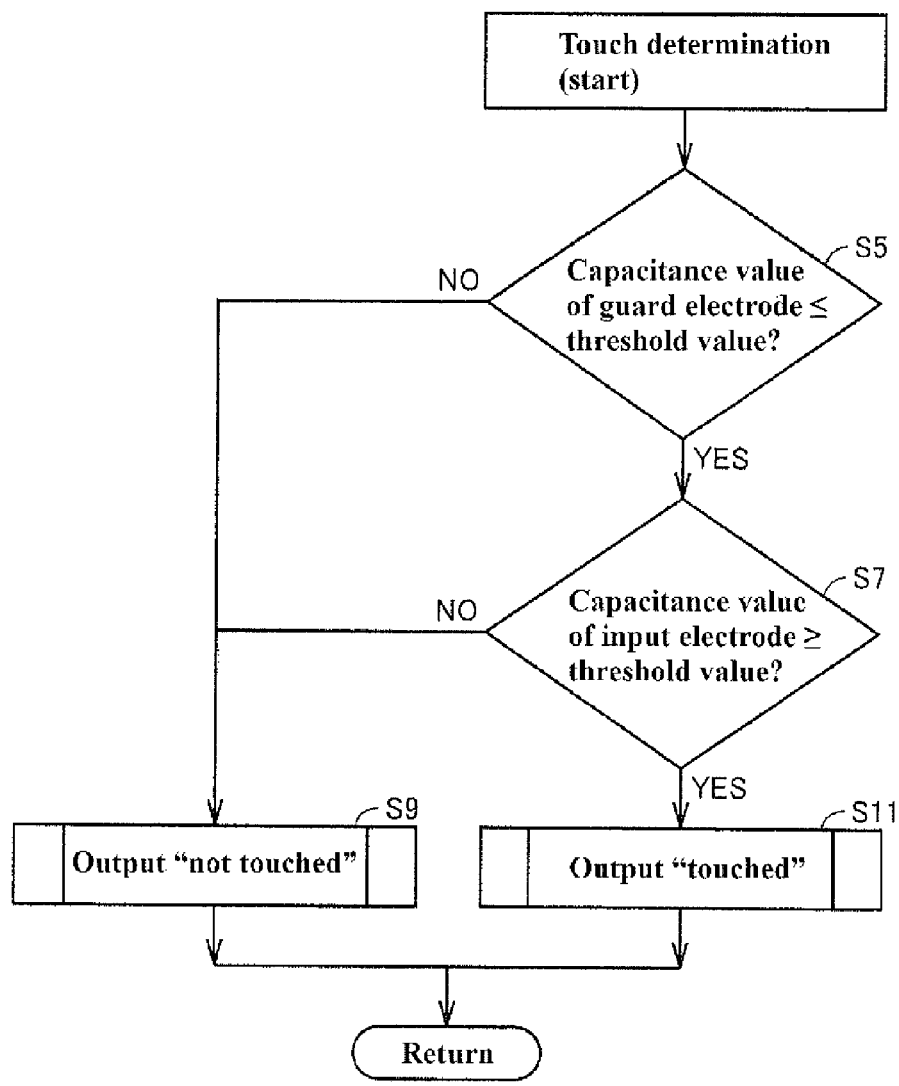
FIG. 7 is a flowchart of processing according to the embodiment.
Figure 8A:
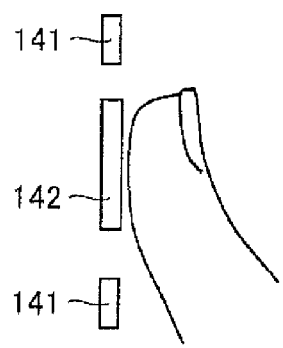
FIGS. 8A and 8B are diagrams illustrating contact with an electrode portion according to the embodiment.
Figure 8B:
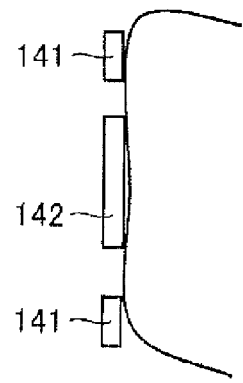
Figure 9A:
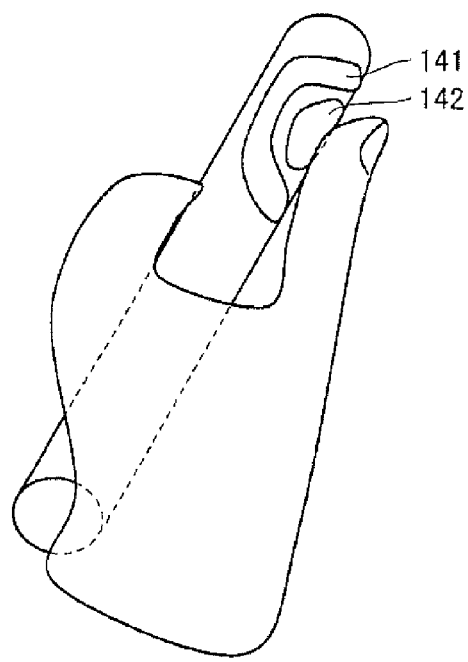
FIGS. 9A and 9B are diagrams illustrating contact with the electrode portion according to the embodiment.
Figure 9B:
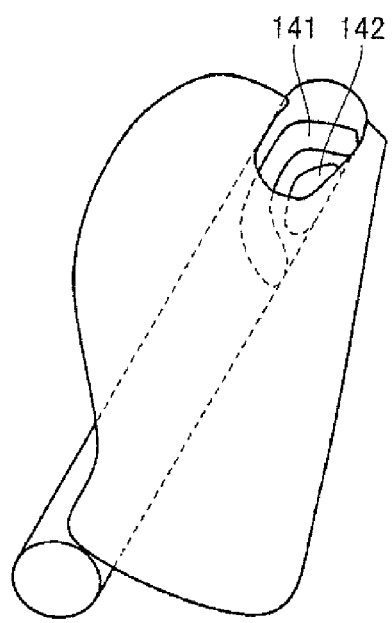

FIGS. 6 and 7 show flowcharts of processing according to the present embodiment. These flowcharts are stored as programs in the memory 121 in advance, and the CPU 120 reads out these programs from the memory 121 and executes them. FIGS. 8 and 9 show examples of how the switch 124 is touched by a finger.

As shown in FIG. 6, the operation reception unit 133 makes a touch determination regarding whether or not the switch 124 was touched by a finger (conductor) (step T1). If "not touched" is output as a result of the determination (NO in step T3), the control unit 130 repeats the processing of step T1, and if "touched" is output (YES in step T3), the procedure moves to step T5.

If "touched" was output, the output control unit 134 controls the output unit 16 so as to output audio, light, or the like for a certain time period in a predetermined manner (step T5). Accordingly, the user is notified that for a certain time period, operations will be received if the switch 124 is operated.

Note that the manner of notification is not limited to this, and a configuration is possible in which the electric toothbrush 1 has multiple types of operation modes, and in step T5, the control unit 130 performs control such that upon reception of a first operation for which "touched" was determined, that fact is notified by switching the operation mode from before the reception of the operation to another type of operation mode for a certain time period. More specifically, the notification is made by changing the vibration frequency of the brush part 21 by changing the drive signal supplied to the motor 10 as described above to a frequency that corresponds to the operation mode to which the electric toothbrush 1 was switched.

The operation reception unit 133 determines whether or not the pattern of output from the capacitance-type sensor 143 matches a predetermined pattern in the aforementioned certain time period (NO in step T7 and step T9). For example, the operation reception unit 133 detects the pattern of change in the capacitance value of the input electrode 142 indicated by the output from the capacitance-type sensor 143, compares the detected pattern of change to a pattern of change that corresponds to a predetermined operation, and determines whether or not the predetermined operation was performed based on the result of the comparison. Examples of the predetermined operation include a single tap, a double tap, and a slide operation, and the determination regarding the predetermined operation will be described in detail later.

If it is determined that a predetermined operation was performed in the certain time period (YES in step T7), the operation reception unit 133 analyzes that predetermined operation and outputs an operation instruction based on the result of the analysis (step T11). In this way, input determination is performed. Specifically, it is determined that the user input an operation instruction for controlling the operation (rotation frequency of the motor 10 or the like) of the electric toothbrush 1 in accordance with the content of the operation received by the operation reception unit 133.

On the other hand, if it is determined that an operation corresponding to a predetermined pattern was not performed in the certain time period (NO in step T7, YES in step T9), the operation reception unit 133 does not perform input determination (step T13).

Note that when the certain time period has elapsed, the output of audio is stopped, the light is extinguished, or the operation mode is returned to the original operation mode (operation mode from before the switch).

The following describes the touch determination processing (step T1) in FIG. 6 with reference to FIG. 7.

First, the operation reception unit 133 compares the capacitance value of the guard electrode 141 included in the output from the capacitance-type sensor 143 with a first threshold value for the touch determination, and determines whether or not the guard electrode 141 was touched by a conductor based on the result of the comparison (step S5). Specifically, if it is determined based on the result of the comparison that the condition "capacitance value≤first threshold value" is satisfied (YES in step S5), the procedure moves to the later-described processing of step S7, and if it is determined that this condition is not satisfied (NO in step S5), "not touched" is output (step S9).

If the electrode portion of the switch 124 is configured by only the input electrode 142, the determination in step S5 is made using the capacitance value of the input electrode 142.

In step S7, the operation reception unit 133 compares the capacitance value of the input electrode 142 included in the output from the capacitance-type sensor 143 with a second threshold value for the touch determination, and determines whether or not the input electrode 142 was touched by a conductor based on the result of the comparison (step S7). Specifically, if it is determined based on the result of the comparison that the condition "capacitance value≥second threshold value" is satisfied (YES in step S7), "touched" is output (step S11). If it is determined that this condition is not satisfied (NO in step S7), "not touched" is output (step S9).

Note that although it is envisioned that the first and second threshold values are stored in a predetermined area of the memory 121 in advance, the determination references are not limited to being measured capacitance values, and instead may be a rate of change in the capacitance value per unit of time (e.g., +10 pf/sec), or may be a combination of the two.

According to the processing shown in FIGS. 6 and 7, if a finger intentionally touches only the input electrode 142 as shown in (A) of FIG. 8 and (A) of FIG. 9, it is determined that the guard electrode 141 was not touched, and the determination result is "touched" for the input electrode 142, and therefore a first operation is received. By performing the input determination from step T5 onward in FIG. 6 in this case, it is possible to receive an intentional operation (a second operation that corresponds to a predetermined pattern in the certain time period) performed on the switch 124, and control the operation of the electric toothbrush 1 in accordance with the content of the operation. On the other hand, if the switch 124 is unintentionally touched by a finger or palm as shown in (B) of FIG. 8 and (B) of FIG. 9, it is determined that the guard electrode 141 was touched, but the determination result is "not touched" for the input electrode 142, and therefore the input determination from step T5 onward in FIG. 6 is not performed. This enables preventing a false operation such as the user unintentionally touching the switch 124.

Electrode Arrangement

With the switch 124 of the present embodiment, the guard electrode 141 serving as a second electrode is arranged in the periphery of the input electrode 142 serving as a first electrode.

Figure 10A:
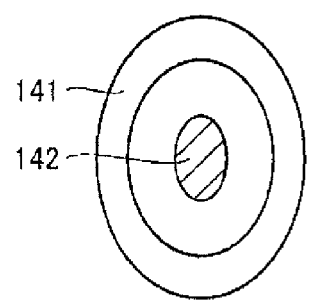
FIGS. 10A, 10B and 10C are diagrams showing examples of arrangements of electrodes in the switch according to the embodiment.
Figure 10B:
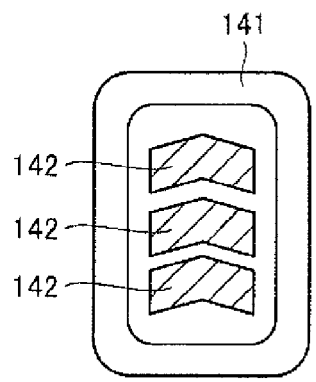
Figure 10C:
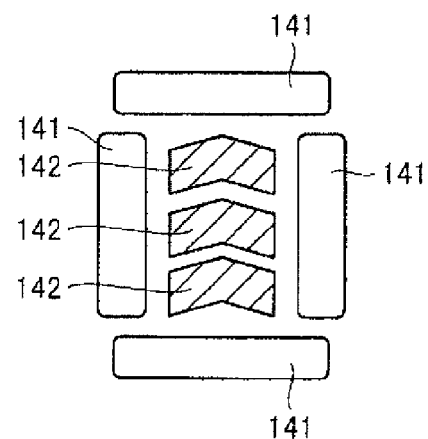

FIG. 10 shows examples of arrangements of electrodes in the switch 124. In (A) of FIG. 10, one circular guard electrode 141 is arranged in the periphery of the input electrode 142, so as to surround the input electrode 142.

In (B) of FIG. 10, one rectangular guard electrode 141 is arranged in the periphery of multiple input electrodes 142 arranged in a row, so as to surround the input electrodes 142. The slide operation, which is one type of the aforementioned second operation, is an operation in which a finger is slid in the same direction as the direction in which the row of aligned input electrodes 142 extends.

A configuration is possible in which the rectangular guard electrode 141 shown in (B) of FIG. 10 is obtained by arranging separate guard electrodes 141 so as to correspond to the sides of the rectangle, as shown in (C) of FIG. 10. In (C) of FIG. 10, the guard electrodes 141 corresponding to the respective sides have the same shape and size (electrode area) as each other, and the input electrodes 142 also have the same shape and size (electrode area) as each other. Accordingly, the capacitance values of the electrodes will match each other if the area of contact with the conductor on the electrode surface is the same, thus making the touch determination easy to make.

Shapes of Portion Corresponding to Electrodes

The portions of the casing that correspond to the guard electrode 141 and the input electrode 142 are given different shapes as shown in FIGS. 11 to 15 so that when the user holding the body portion 2 during brushing touches the switch 124 with their finger while brushing their teeth, the user can easily distinguish between the input electrodes 142 and the guard electrodes 141 by tactile sensation.

In FIGS. 11 to 15, (A) schematically show the cross-sectional shape of the portions of the casing where the guard electrode 141 and the input electrode 142 are arranged, the cross-section being taken along the lengthwise direction of the body portion 2, and FIGS. 11 to 15, (B) schematically show the surface of the portions of the casing that correspond to those in (A) of FIGS. 11 to 15.

Figure 11A:
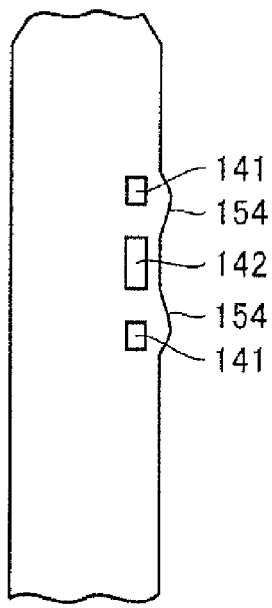
FIGS. 11A and 11B are diagrams showing the shape of a portion corresponding to electrodes on the casing according to the embodiment.
Figure 11B:
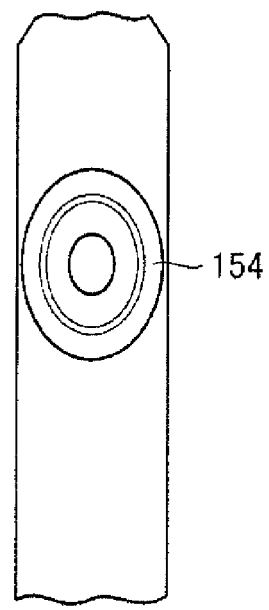
Figures 12A, 12B:
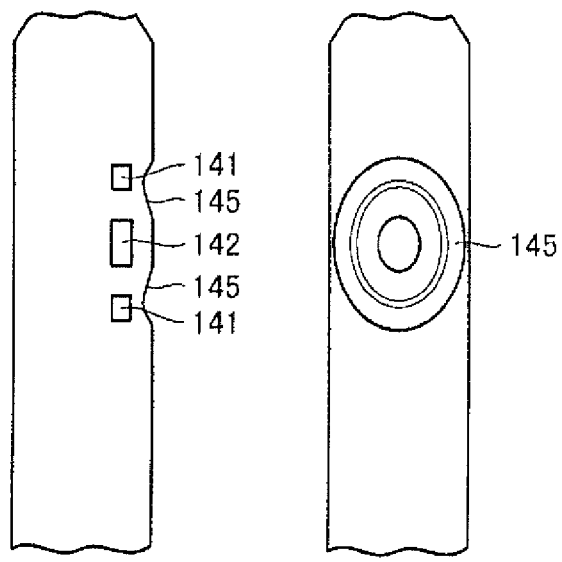
FIGS. 12A and 12B are diagrams showing the shape of a portion corresponding to electrodes on the casing according to the embodiment.

In FIG. 11, a protrusion portion 154 made of a resin material is formed in the portion of the casing surface that corresponds to the guard electrode 141, whereas a recession portion 145 is formed in FIG. 12. This allows the positions of the guard electrode 141 and the input electrode 142 to be distinguished from each other by touching them with the finger.

Figures 13A, 13B:
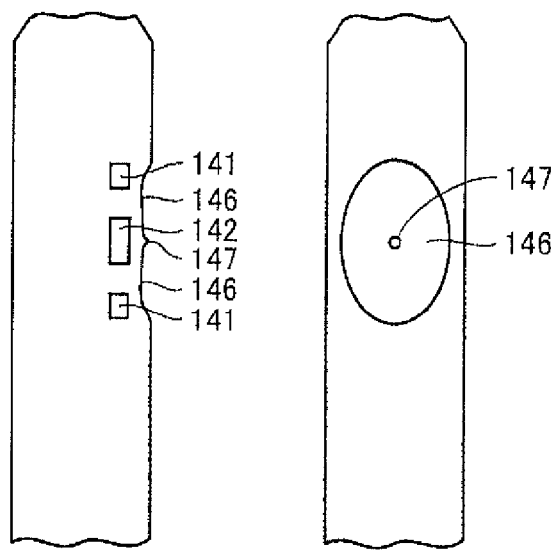
FIGS. 13A and 13B are diagrams showing the shape of a portion corresponding to electrodes on the casing according to the embodiment.

The face where the switch 124 is provided on the surface of the casing is a curved face, and in FIG. 13, a flat face 146 is formed in only the portion where the switch 124 is provided, and a small protrusion portion 147 is formed in the portion of the flat face 146 that corresponds to the input electrode 142. This enables the position of the switch 124 and the position of the input electrode 142 on the switch 124 to be distinguished from each other by touching them with the finger.

Figures 14A, 14B:
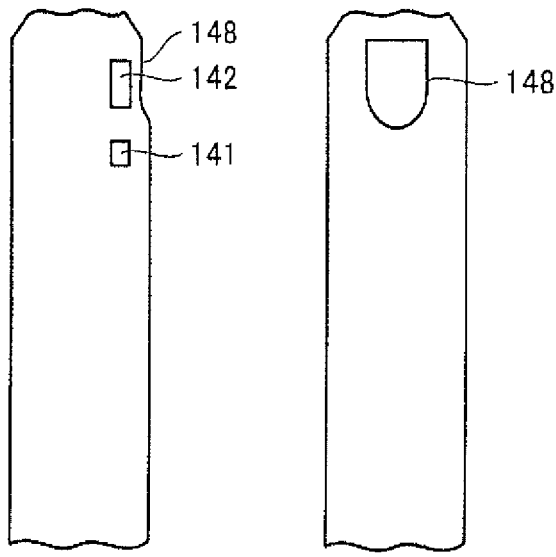
FIGS. 14A and 14B are diagrams showing the shape of a portion corresponding to electrodes on the casing according to the embodiment.
Figures 15A, 15B:
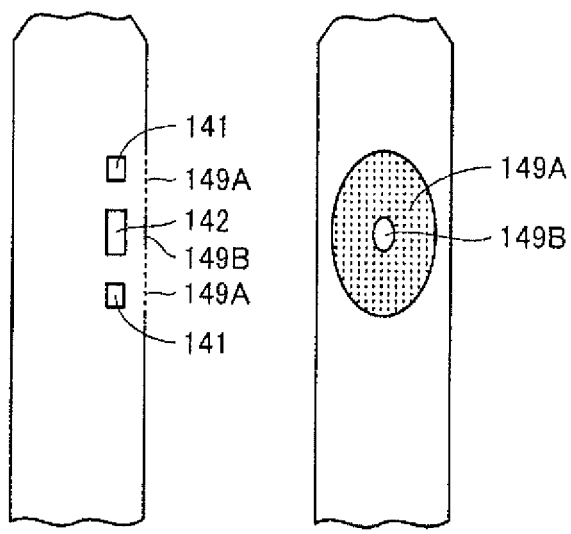
FIGS. 15A and 15B and are diagrams showing the shape of a portion corresponding to electrodes on the casing according to the embodiment.

In FIG. 14, the input electrode 142 is arranged at the edge of the body portion 2, and a flat face 148 is formed in only the portion of the casing surface where the input electrode 142 is provided. The flat face 148 has a semicircular shape whose flat side is on the end portion side. In FIG. 15, a fine protrusion-recession pattern 149A achieved by texture (fine protrusions and recessions) processing is formed in the portion of the casing surface that corresponds to the guard electrode 141, and a flat face 149B is formed in the portion that corresponds to the input electrode 142.

The shapes shown in FIGS. 14 and 15 can be formed in the step for forming the casing of the body portion 2 if the shapes are directly formed in the tube-shaped mold, thus making it possible to reduce costs associated with dies and molding.

Examples of Electrode Arrangements

Figures 16A, 16B:
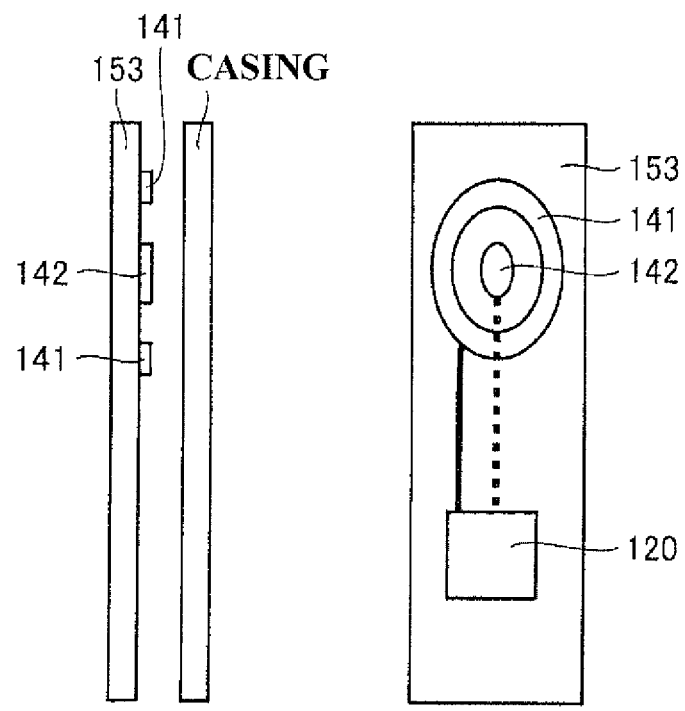
FIGS. 16A and 16B are diagrams showing an example of the arrangement of electrodes in relation to a substrate according to the embodiment.

FIGS. 16 to 19 shows examples of arrangements of the electrodes of the switch 124. In FIG. 16, (A) schematically shows the cross-sectional shape of the portion of the casing where the guard electrode 141 and the input electrode 142 are arranged, the cross-section extending in the lengthwise direction of the body portion 2. In FIG. 16, (B) shows the wiring pattern between the CPU 120 and the electrodes on a substrate 153 in (A) of FIG. 16.

As shown in (A) of FIG. 16, the CPU 120 and the like, which are housed inside the casing, are mounted on the substrate 153, and an electrode pattern including the guard electrode 141 and the input electrode 142 is formed on the principal face of the substrate 153. The substrate 153 is housed inside the casing such that the principal face opposes the inner face of the casing. In this case, it is difficult to precisely measure the capacitance due to the space (distance) between the electrode pattern and the casing.

Figure 17:
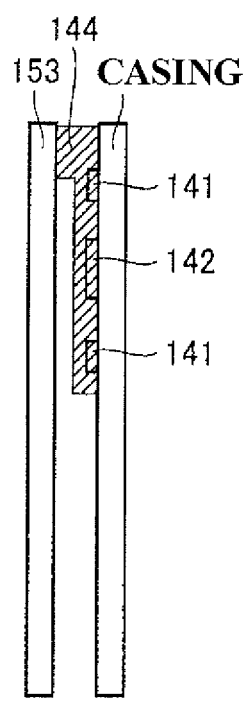
FIG. 17 is a diagram showing an example of the arrangement of electrodes in relation to the substrate according to the embodiment.
Figure 18:
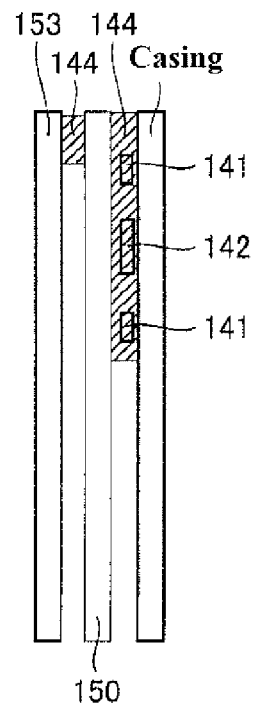
FIG. 18 is a diagram showing an example of the arrangement of electrodes in relation to the substrate according to the embodiment.

FIGS. 17 and 18 show other examples of arrangements for obtaining precision in the measurement of the capacitance. In FIG. 17, the electrode pattern is arranged on the inner face of the casing instead of on the substrate 153. Specifically, an electrode pattern including the guard electrode 141 and the input electrode 142 is formed on a conductive seal 144 using an ITO (Indium Tin Oxide) film as the transparent electrode film, and the seal 144 is affixed to the inner face of the casing. Part of the seal 144, which is affixed to the inner face of the casing, is drawn out and connected to a wiring pattern on the principal face of the substrate 153. In this case, it is difficult to precisely measure the capacitance because the electrode pattern is directly formed on the inner face of the casing.

In FIG. 18, the substrate 153 is housed inside the casing so as to be separated from other circuit portions using a conductive chassis 150. The principal face of the substrate 153 opposes the inner face of the casing with the chassis 150 interposed therebetween. An electrode pattern including the guard electrode 141 and the input electrode 142 is formed on the conductive seal 144, and the seal 144 is affixed to the front surface of the chassis 150 that opposes the inner face side of the casing. A portion of the seal 144 that is affixed to the rear surface of the chassis 150 (i.e., the surface that opposes the principal face of the substrate 153) is connected to a wiring pattern on the principal face of the substrate 153. This enables the guard electrode 141 and the input electrode 142 to be electrically conductive with the wiring pattern on the substrate 153 via the seal 144 and the chassis 150.

Figure 19:
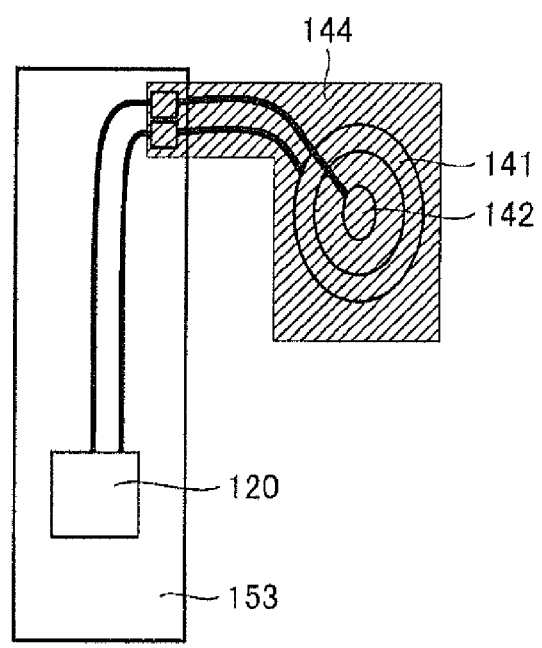
FIG. 19 is a diagram showing an example of the arrangement of electrodes in relation to the substrate according to the embodiment.

FIG. 19 shows an example of a wiring pattern for achieving electrical conduction between the electrodes (the guard electrode 141 and the input electrode 142) and the CPU 120 on the principal face of the substrate 153 using the seal 144 on which an electrode pattern including the guard electrode 141 and the input electrode 142 is formed as shown in FIGS. 17 and 18.

Operation Pattern Detection

FIGS. 20 to 22 show examples of the detection of an operation pattern of the second operation type based on change in the capacitance values of a row of input electrodes 142. In these figures, a row of input electrodes 142 aligned in a single row is shown at the top, and a graph of capacitance values is shown at the bottom. The horizontal axis in the graph shows positions in the row of electrodes that correspond to the input electrodes 142 at the top, and the vertical axis shows the measured capacitance values.

Based on the output from the capacitance-type sensor 143, the operation reception unit 133 detects the type of operation based on the pattern of change in the capacitance values of the row of input electrodes 142 of the switch 124. Detection operations will be described with reference to FIGS. 20 to 22.

Note that here, separate wiring patterns are formed between the capacitance-type sensor 143 and each of the input electrodes 142, the capacitance-type sensor 143 has an input port for each of the wires, and the input ports are respectively connected to the wires. Accordingly, the capacitance-type sensor 143 can identify the port numbers based on change in the potential at the input ports. By identifying port numbers, it is possible to uniquely identify corresponding positions in the row of input electrodes 142.

Firstly, the case of detecting the position where an operation is performed in the row of input electrodes 142 will be described with reference to FIG. 20. In FIG. 20, (A) and (B) show normal detection, and (C) shows detection when there is exposure to water.

In (A) of FIG. 20, input determination is not performed since the capacitance value measured at each of the input electrodes 142 in the row is less than the above-described second threshold value (the value indicated by the broken line in the graph), whereas input determination is performed in (B) of FIG. 20 since the capacitance value measured at one or more of the input electrodes 142 in the row is greater than or equal to the second threshold value. In (B) of FIG. 20, among the input electrodes 142 at which the measured capacitance value is greater than or equal to the second threshold value, the position of the input electrode 142 having the highest capacitance value is determined to be the position of the finger. In this input determination, the capacitance-type sensor 143 outputs the input port numbers and the measured capacitance values via the corresponding ports. Accordingly, the operation reception unit 133 identifies the port numbers at which the measured capacitance value is greater than or equal to the second threshold value. Based on the pattern of temporal change in the capacitance value of the input port with the same identified port number, it is determined whether the pattern of change is a single-tap pattern or a double-tap pattern.

In contrast, input determination is not performed in the case where the measured capacitance value is greater than or equal to the second threshold value at multiple input electrodes 142 in the row due to being exposed to water or the like, as shown by the pattern shown in (C) of FIG. 20.

Accordingly, it is possible to generate an operation instruction that corresponds to a single tap or double tap on the row of input electrodes 142, and to control the operation of the electric toothbrush 1 in accordance with the generated operation instruction.

Note that it is determined whether a single-tap operation or a double-tap operation was performed as follows. Specifically, when a first tap is detected in the certain time period, it is determined that the second operation is a "single-tap operation", and if a second tap operation is detected within a predetermined time period from the first tap operation, it is re-determined that the second operation is a "double-tap operation". Note that if the first tap is detected immediately before the end of the certain time period, the second tap will be detected outside the certain time period, but in the present embodiment, it is determined that the second operation is the "double-tap operation" even in such a case. In other words, if the first tap is detected in the certain time period, and the second tap is detected within the predetermined time period from the first tap, then it is determined that the second operation is the "double-tap operation".

Next, the slide operation will be described with reference to FIG. 21. The slide operation is detected based on a velocity V of the slide movement of the finger on the row of input electrodes 142.

In FIG. 21, (A) shows the case where input determination is not performed, similarly to the case shown in (A) of FIG. 20. In FIG. 21, (B) to (D) show movement of the peak value of the capacitance value that occurs in conjunction with the movement of the finger in the slide operation. When the slide operation is performed, the peak value of the capacitance value necessarily moves between adjacent input electrodes 142 in the change in capacitance value, and the velocity of the movement of the peak value is greater than or equal to a certain velocity.

The operation reception unit 133 detects the velocity of change in the port number at which the peak value is measured, and upon determining that the detected velocity is greater than or equal to a certain velocity, determines that the slide operation was performed, and outputs an operation instruction that corresponds to the slide operation.

Here, assume that the numerical values of the port numbers corresponding to the row of input electrodes 142 sequentially increase with the arrangement of the input electrodes 142 in the row (e.g., increase in the rising order of 1, 2, 3, 4, 5, and so on). Accordingly, it is possible to calculate the amount (distance) of movement per unit of time based on the amount of increase per unit of time in the numerical value that expresses the port number at which the peak value was measured, and to calculate the movement velocity of the peak value. If it is determined that the movement velocity is greater than or equal to a certain velocity, it is determined that the slide operation was performed.

Note that even with the same slide operation, there may be different types of operation instructions for switching the operation mode depending on the movement velocity of the peak value, even with the same slide operation, there may be different types of operation instructions for switching the operation mode depending on the movement direction of the peak value, and even with the same slide operation, there may be different types of operation instructions depending on combinations of the movement velocity and direction.

Also, as shown in FIG. 22, even when the row of input electrodes 142 is exposed to water, it is possible to detect the velocity V of the slide movement, that is to say, the movement velocity of the peak value. Specifically, the switch 124 tends to be exposed to water since the electric toothbrush 1 is used in an environment where it tends to be exposed to water, such as a washroom. For example, there are cases where the row of input electrodes 142 is exposed to water as shown in (A) to (D) of FIG. 22. Even in such a case, position detection can be performed in (B) to (D) of FIG. 22. Specifically, in (B) to (D) of FIG. 22, the volume of the finger in contact with the input electrodes 142 is greater than that of the water in contact, and therefore the measured capacitance value is higher with the finger than with the water, and the peak value of the capacitance value resulting from contact with the finger (see the wide arrow in the figures) can be detected. Since the peak value can be detected, it is possible to detect the operation position, and to detect the movement velocity of the peak value as well. This enables determining whether or not the slide operation was performed.

Figure 23:
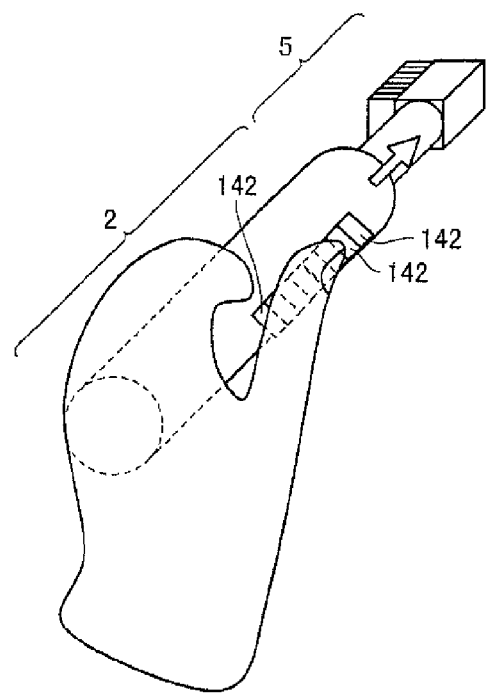
FIG. 23 is a diagram showing an example of how input electrodes are aligned in a row according to the embodiment.
Figure 24:
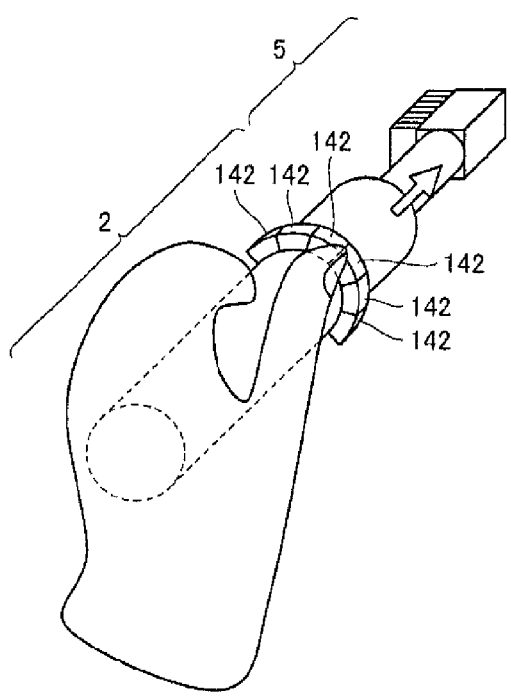
FIG. 24 is a diagram showing another example of how input electrodes are aligned in a row according to the embodiment.

As examples in which the input electrodes 142 are aligned in a row, FIG. 23 shows an example in which the input electrodes 142 are aligned in a row in the same direction as the lengthwise direction of the body portion 2 indicated by the arrow, and FIG. 24 shows an example in which the input electrodes 142 are aligned in a row along the periphery of the column of the body portion 2 so as to extend in a direction that intersects (including being orthogonal to) the lengthwise direction indicated by the arrow.

Function for Preventing Influence from Water

Figure 26A:
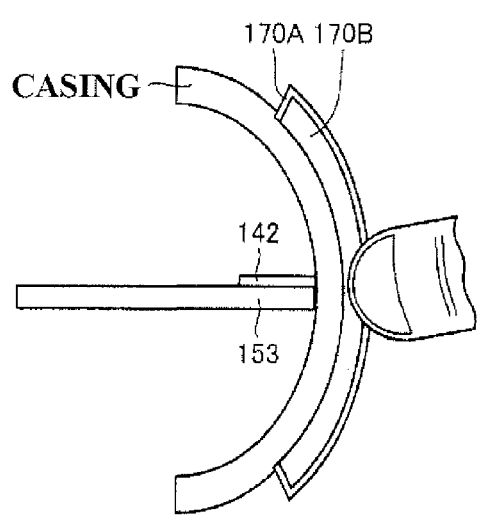
FIGS. 26A and 26B are diagrams illustrating a function for preventing the influence of water on the electrode portion according to the embodiment.
Figure 26B:
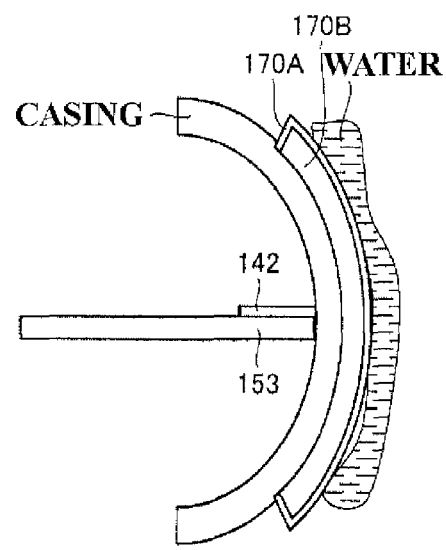

The following describes a function for preventing influence from water on the electrode portion of the switch 124 in the present embodiment with reference to FIGS. 25 and 26.

In FIG. 25, (A) shows a state in which the portion where the switch 124 is arranged on the surface of the casing of the body portion 2 is covered by a cover member 170, and (B) shows a cross-section of the portion covered by the cover member 170, taken along a direction orthogonal to the lengthwise direction of the body portion 2. The electrode portion is arranged at the end portion of the substrate 153 that is in the vicinity of the inner face of the casing so as to be adjacent to the casing as shown in (A) of FIG. 16.

In order to maintain precision in the measurement of the capacitance even if the electrode portion of the switch 124 is exposed to water, the electrode portion that includes the guard electrode 141 and the input electrode 142 is covered by, for example, a film 170A and a sponge 170B made of a resin material that has plasticity (the property of returning to the original shape when an external deforming force is removed). Accordingly, even if there is exposure to water, the distance between the water and the electrode portion increases by an amount corresponding to the thickness of the sponge 170B, thus making it possible to reduce the change in the capacitance and reduce the influence of the water (see (B) of FIG. 26).

Although water does not produce enough pressing force to flatten the sponge 170B, the sponge 170B is flattened (compressed) by pressing force from a finger. Accordingly, the distance between the finger and the electrode portion on the substrate 153 inside the casing can be reduced even if the sponge 170B is interposed therebetween, and it is possible to measure the capacitance value in order to determine the type of operation (see (A) of FIG. 26).

Also, in order to further reduce the influence of water, the film 170A having plasticity may be given water-repellent properties.

In this way, the electric toothbrush 1 of the present embodiment includes the body portion 2, a portion of which is gripped by the user, and the brush part 21 that is exchangeably attached to the body portion, wherein the body portion 2 includes a contact-type sensor unit that is the switch 124 that is arranged on a portion of the body portion 2 that excludes the gripped portion, and that receives an operation from the outside, and includes a control unit 130 for controlling operations of the electric toothbrush 1 in accordance with an operation received by the contact-type sensor unit. The control unit 130 outputs an indication that operations can be received for a certain time period if a first operation is received by the contact-type sensor unit. Also, if a second operation received in the certain time period is an operation that corresponds to a predetermined pattern, the control unit 130 controls operations of the electric toothbrush 1 in accordance with the second operation.

The embodiment disclosed here is to be considered as an example in all respects and not as limiting in any way. The scope of the present invention is defined by the claims, not the above description, and all changes that come within the meaning and range of equivalency of the claims are intended to be embraced therein.

REFERENCE SIGNS LIST

1 Electric toothbrush
2 Body portion

10 Motor
16 Output unit
21 Brush part
130 Control unit
133 Operation reception unit
134 Output control unit
141 Guard electrode
142 Input electrode
143 Capacitance-type sensor
144 Seal
145 Recession portion
146,148,149B Flat face
147,154 Protrusion portion
149A Protrusion-recession pattern
150 Chassis
153 Substrate
170 Cover member
170A Film
170B Sponge
124 Switch

The invention claimed is:

1. An electric toothbrush comprising:
a body portion, a portion of which is gripped by a user; and
a brush portion that is exchangeably attached to the body portion,
wherein the body portion includes
a contact-type sensor unit that is arranged on a portion of the body portion that excludes the gripped portion, and is for receiving an operation from the outside, and
a control unit for controlling operation of the electric toothbrush in accordance with the operation received by the contact-type sensor unit,
in a case where a first operation is received by the contact-type sensor unit, the control unit outputs an indication that an operation can be received for a certain time period,
in a case where a second operation received by the contact-type sensor unit in the certain time period is an operation that corresponds to a predetermined pattern, the control unit controls operation of the electric toothbrush in accordance with the second operation, and wherein:
a slide operation corresponds to the predetermined pattern,
the control unit includes an operation reception unit, and
based on a pattern of change in output from the contact-type sensor unit, the operation reception unit determines whether or not the second operation received in the certain time period is an operation that corresponds to the predetermined pattern.

2. The electric toothbrush according to claim 1,
wherein the body portion has a columnar shape, and
the portion that excludes the gripped portion is an end portion in a lengthwise direction of the columnar shape of the body portion.

3. The electric toothbrush according to claim 1,
wherein a plurality of different types of operations correspond to the predetermined pattern, and
the control unit determines the type of the second operation that was received by the contact-type sensor unit in the certain time period, and controls operation of the electric toothbrush in accordance with the determined type of operation.

4. The electric toothbrush according to claim 1,
wherein the electric toothbrush has a plurality of types of operation modes, and
when the first operation is received, the control unit outputs an indication that an operation can be received by switching the operation mode.

5. The electric toothbrush according to claim 1,
wherein the contact-type sensor unit includes an electrode portion,
the operation reception unit includes a capacitance sensor that measures a capacitance value of the electrode portion, and
the operation reception unit compares the capacitance value measured by the capacitance sensor and a first threshold value, and determines based on a result of the comparison whether or not an operation from the outside is the first operation.

6. The electric toothbrush according to claim 5, wherein the operation reception unit compares the capacitance value of the electrode portion measured by the capacitance sensor and a second threshold value, and determines based on a result of the comparison whether or not an operation from the outside is the second operation.

7. The electric toothbrush according to claim 6,
wherein the electrode portion includes an input electrode and a guard electrode that is arranged so as to be in a periphery of the input electrode,
there are a plurality of the input electrodes aligned in one row, and
the second operation exhibits a pattern of temporal change in the capacitance values measured at the plurality of aligned input electrodes.

8. The electric toothbrush according to claim 5,
wherein the contact-type sensor unit is housed inside a casing of the body portion, and
a portion of an external surface of the casing that corresponds to the electrode portion arranged inside the casing has a cover portion that covers the portion of the external surface and is made up of a member that has plasticity.

* * * * *